United States Patent [19]
Bommer

[11] 3,977,008
[45] Aug. 24, 1976

[54] METHOD AND AN APPARATUS FOR DETECTING AND RECORDING THE NUMBER OF PHENOMENA

[75] Inventor: Paul Bommer, Breitenbach, Switzerland

[73] Assignee: Zumbach Electronic-Automatic, Orpund, Switzerland

[22] Filed: Dec. 16, 1974

[21] Appl. No.: 533,266

Related U.S. Application Data

[62] Division of Ser. No. 347,320, April 6, 1973, Pat. No. 3,883,878.

[30] Foreign Application Priority Data
Apr. 10, 1972 Switzerland............................ 5258/72

[52] U.S. Cl. .................................. 346/1; 346/33 F
[51] Int. Cl.² ........................................... G01D 9/30
[58] Field of Search ............... 346/1, 49, 33 F, 113; 324/54

[56] References Cited
UNITED STATES PATENTS

| | | | |
|---|---|---|---|
| 2,746,834 | 5/1956 | McLean | 346/113 |
| 3,359,562 | 12/1967 | Staubli | 346/49 X |
| 3,413,541 | 11/1968 | Swim et al. | 324/54 |

*Primary Examiner*—Joseph W. Hartary

[57] ABSTRACT

A method and an apparatus for detecting and recording the number of phenomena, for instance of defects of a product continuously manufactured, wherein a graphic record is made on a recording tape in a direction transverse to the advancing direction of said recording tape and at a length corresponding to the sum of unit steps of which the number is equal to the number of phenomena occurring during a measuring or counting period, a fixed limited number of unit steps being executed and thereby a record of a fixed length produced upon failure of detecting means for said phenomena.

6 Claims, 12 Drawing Figures

METHOD AND AN APPARATUS FOR DETECTING AND RECORDING THE NUMBER OF PHENOMENA

CROSS REFERENCE

The present application is a division of patent application Ser. No. 347,320, filed Apr. 6, 1973, now U.S. Pat. No. 3,883,878. Priority is claimed from Swiss Pat. No. 5 258/72, filed Apr. 10, 1972, a priority document being in the file of the above patent application Ser. No. 347,320.

BACKGROUND OF THE INVENTION

This invention relates to a method and an apparatus for detecting and recording the number of phenomena occurring during succeeding recording periods, onto a recording tape. The problem of detecting and recording the number of particular phenomena has to be solved in many applications, for instance when checking or supervising a continuous production of various products, when counting traffic and in many further cases of statistic evaluation of events and phenomena.

Various apparatus for detecting and recording phenomena are known wherein graphs are recorded, the length of each graph corresponding to the number of phenomena detected by one detecting unit during a predetermined measuring period or while testing a predetermined length of a product, for instance an enamelled wire. Such graphs are preferably recorded on a recording tape in a direction transversal to the advancing direction of the recording tape which is stepwise advanced at the end of each recording period. Since the phenomena recorded usually occur at random, the length of the individual graphs recorded on the tape varies, that is, the number of phenomena recorded during each test period is subject to changes. However, if no phenomena are recorded during a number of periods, it is impossible to conclude clearly from this fact, whether no phenomena have occurred or whether the detecting and/or recording apparatus is defectuous.

SUMMARY OF THE INVENTION

It is an object of this invention to make use of the above fact that normal graphs recorded during successive test periods practically always change in length, for obtaining a clear information on whether the detecting and recording apparatus and/or the producing plant supervised by the apparatus properly operates or not. According to this invention a feeler is provided for sensing an event and for detection of phenomena occurring within said event, said feeler being continuously supervised and upon failure of the feeler and of the event a record indicating said failure is effected during each recording period, in that the same limited number of phenomena is automatically produced and recorded during each recording period. Therefore, if graphs of the same length appear on the recording tape for several succeeding test periods, the operator may conclude from this fact that this constant length of the graphs is not normal and that something is wrong. The operator may then find out the reasons for the failure and repair the damage.

This invention will now be explained in detail with reference to two embodiments of the apparatus for recording the number of breakdowns through the insulation of enamelled or varnished wires during manufacture thereof.

Figure 3:
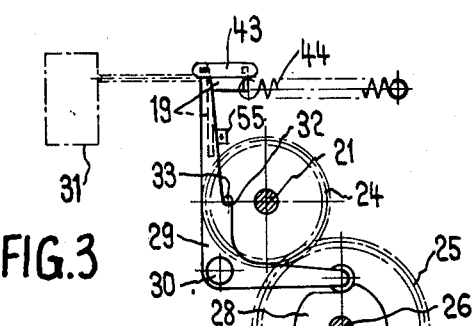
FIG. 3 is a section view of the recorder.
Figure 4:
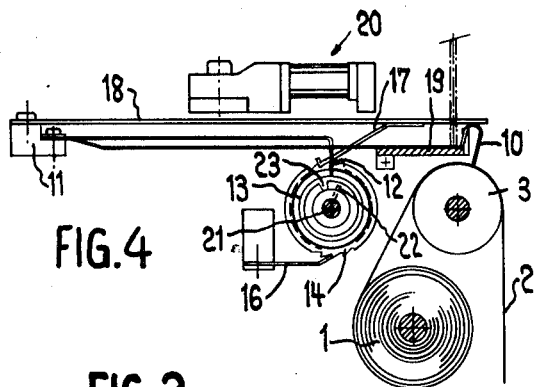
FIG. 4 shows parts of a zero setting device.
Figure 1:
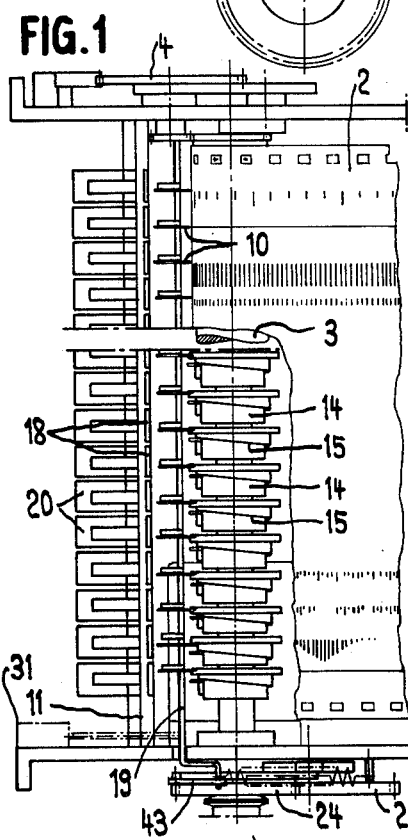
FIG. 1 is a front view of a recorder of the one embodiment of the apparatus.
Figure 2:
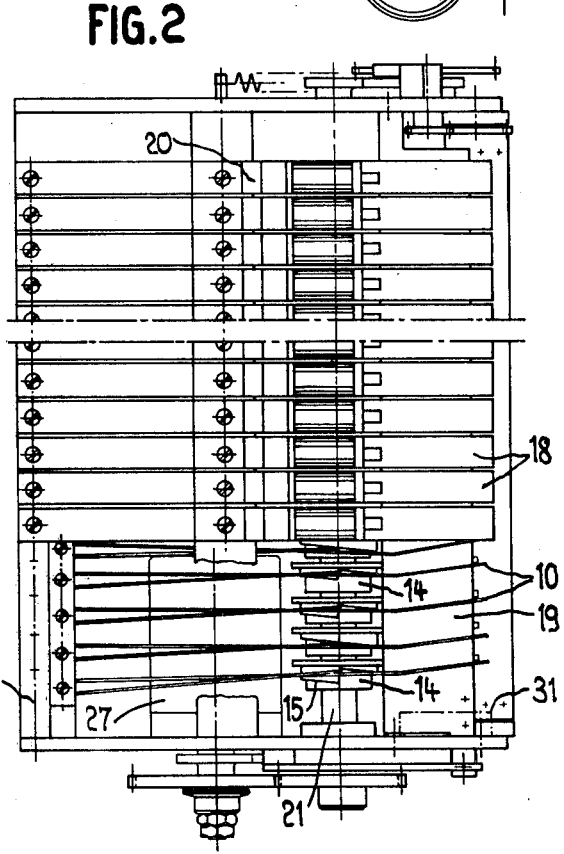
FIG. 2 is a top view onto the recorder with parts broken away.
Figure 5:
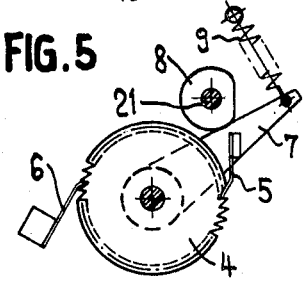
FIG. 5 shows parts of a stepping device.

As may be seen from FIGS. 1 to 3, the recorder of the apparatus has a paper roll 1 from which the paper tape or recording tape 2 is pulled off over a stepping roller 3. A stepping pawl 5 and a stop pawl 6 engage a ratchet wheel 4 (FIG. 5) fixed at the one end of the shaft of roller 3. The stepping pawl 5 is mounted on a stepping lever 7 pivotably mounted on the shaft of roller 3 and adapted to be actuated by a cam disc 8 against the pull of a spring 9. The driving means for cam disc 8 are described later.

A row of recording pens 10 is disposed above roller 3, graphs or records being produced on a special pressure sensitive paper 2 by pressure of the pens. The recording pens 10 are made of spring steel and form each a loop fixed to a beam 11. The end of each loop which is not writing grips over the writing end and the downwardly bent end 12 engages the writing end of the loop and also a shoulder 13 of a cam disc 14 having a cam surface 15 continuously raising in axial direction outside shoulder 13. When the cam disc 14 rotates the end 12 and therewith also the writing end of the recording pen elastically applied against the cam surface 15 is gradually shifted in axial direction.

Each cam disc 14 has a ratchet toothing at its circumference (FIG. 3), into which engages a stop pawl 16. A stepping spring 17 fixed to a striker spring 18 or made of one piece with the same engages from above the toothing of each cam disc 14. All striker springs 18 are fixed to the beam 11. Their free displaceable ends are located above the writing end of a recording pen 10, these ends of the recording pens also extending over a lifting beam 19 running through below all pens.

An electromagnet 20 is associated with each striker spring 18 for temporarily lifting the striker spring.

All cam disc 14 are mounted for free rotation on a common shaft 21. This shaft has pins 22 associated each with one of the cam disc 14 and serving for adjustment of the cam disc into an initial position in that the pins 22 of the shaft 21 executing an adjusting or resetting rotation engage cams 23 of the cam disc 14 whereby all cam disc are rotated into their initial position in their stepping direction. The toothing at the circumference of the cam disc 14 has a gap the length of which appreciably exceeds one advancing step or one tooth division respectively, such that each cam disc cannot be stepped by its stepping pawl 17 by more than one full revolution.

Adjustment of the cam discs 14 by the shaft 21 is effected by means of a gear illustrated in detail in FIG.

4. A toothed wheel 24 mating with a toothed wheel 25 is fixed on the shaft 21. The toothed wheel 25 is mounted for free rotation on the shaft 26 of a motor 27 but may be driven through a friction coupling. A cam disc 28 is fixed on the motor shaft, this cam disc acting through a roller onto a spring-loaded lever 29 pivotably mounted at 30 and acting through the lifting beam 19 onto a microswitch 31. The lever 29 has a shoulder 32 cooperating with a pin 33 of the toothed wheel 24. The lever 29 is interconnected with the lifting beam 19 by means of a toggle lever 43, the lifting beam being maintained in the illustrated rest position by a spring 44.

The cam disc 8 already described above is fixed at the opposite end of shaft 21.

Figure 6:
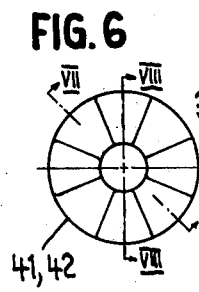
FIG. 6 shows an element of a device for checking proper operation of the production plant.
Figure 7:
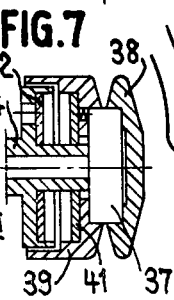
FIGS. 7 and 8 are section views along lines VII—VII and VIII—VIII respectively in FIG. 6.
Figure 8:
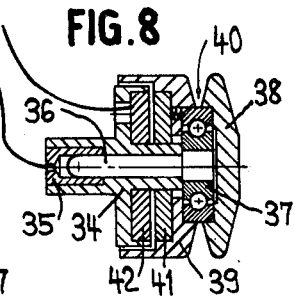

A rotatable test pulley is provided on a separate part of the apparatus, which may be located remote from the recorder, the enameled or varnished wire to be tested being fed over the test pulley. A sleeve 35 is inserted into a stationary part 34 of insulating material, the test voltage which may be in the order of 1000 V being applied to this sleeve. A plug pin 36 which is in electrically conducting connection with the sleeve 35, carries the inner race of a ball bearing 37, a cap 38 and a mantle 39 of insulating material being connected to the outer rim of ball bearing 37. Parts 38 and 39 form a groove 40 between each other, the outer race of the ball bearing 37 being freely accessible at the bottom of this groove. Discs 41 and 42 having raised segments facing each other as shown in FIG. 6 are inserted into parts 34 and 39. A cable or conductor is connected to disc 42. If the disc 41 rotates together with the test pulley, the capacity between discs 41 and 42 varies due to the raised segments thereof, whereby a pulsating signal is induced in disc 42.

Figure 9:
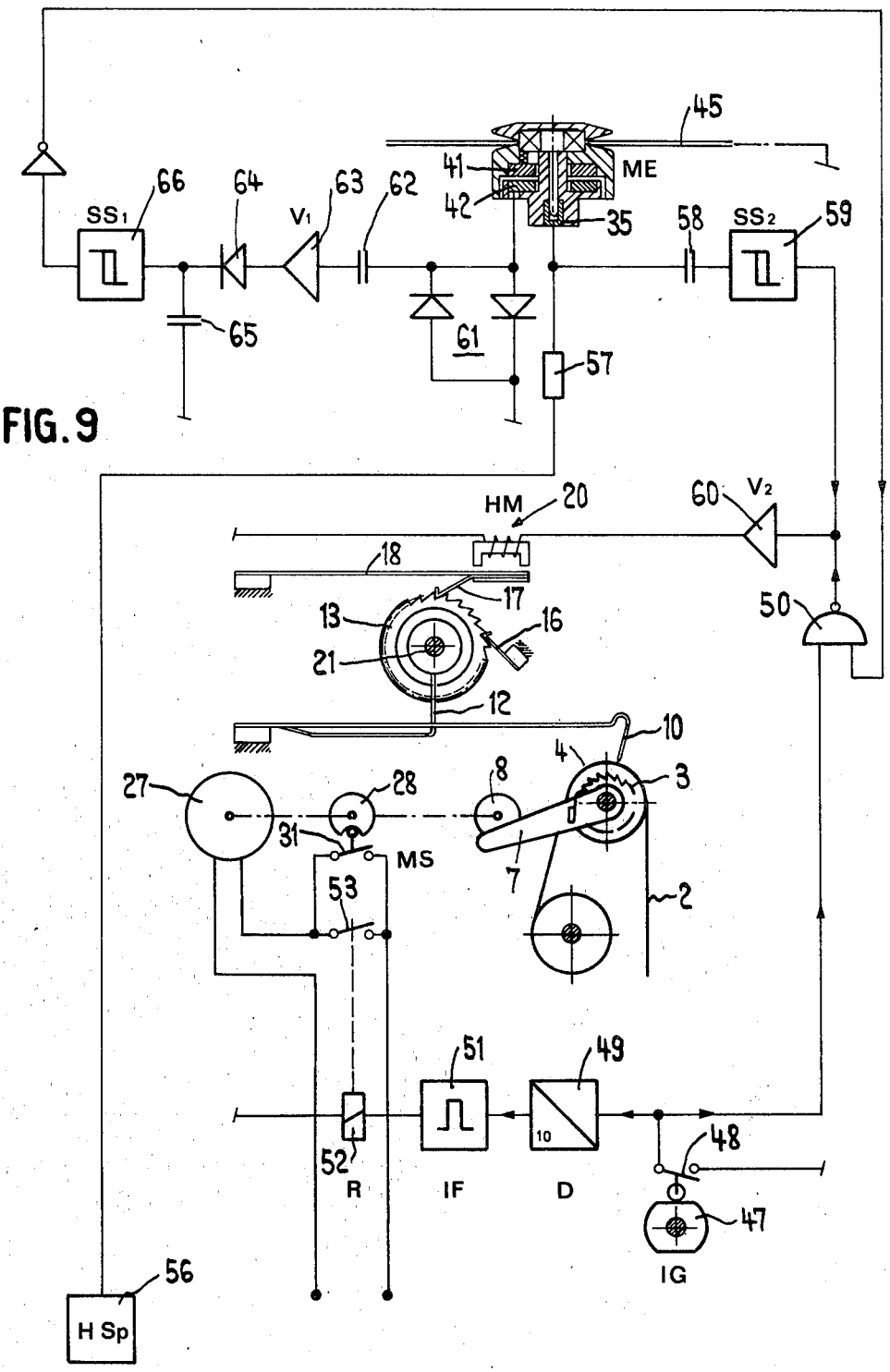
FIG. 9 is a circuit diagram of the essential electrical equipment of the apparatus.

FIG. 9 shows the circuit diagram wherein corresponding parts have the same reference numerals as in FIGS. 1 to 8. The wire 45 is indicated in FIG. 9. Except for the test pulley the apparatus has an odometer located in a suitable position and having a cam disc 47 acting onto a switch 48. As an example, this odometer is so designed that the switch 48 is closed 10 times during passage of 100 meters of wire over a pulley or roller driving the odometer. The switch 48 acts on a pulse counter 49 on one hand and onto the input of a NAND- gate 50 on the other hand. The output of the counter 49 acts through a pulse former 51 onto a relay 52 after reception of 10 pulses, this relay 52 having a making contact 53 in the circuit of the motor 27. The microswitch 31 is connected in parallel with the making contact 53.

The test pulley is energized from a high voltage source 56 through a protecting resistor 57. The test pulley is connected to the input of an amplifier 60 through a condenser 58 and a Schmitt-trigger 59, the output of amplifier 60 acting onto the electromagnet 20. The disc 42 of the test pulley is connected to a limiting circuit 61 and through a condenser 62, an amplifier 63 and a rectifier 64 having a filter condenser 65, to a Schmitt-trigger 66 of which the output is connected to the second input of gate 50. The output of gate 50 acts onto the input of amplifier 60.

During operation each wire of a number of simultaneously produced wires is fed over a test pulley 37 – 40 and the switch 48 is closed by the odometer measuring the length of the wire passing through the test station every time after passage of 10 meters of wire. Upon each passage of a defect of the insulation on the wire a breakdown occurs from the test pulley onto the wire, whereby the voltage at the test pulley breaks down. Through condenser 58 the Schmitt-trigger 59 is reversed and a pulse is transmitted through amplifier 60 to the associated electromagnet 20. Thereby the associated striker spring 18 is lifted and the stepping pawl 17 is shifted back by one tooth in the toothing of the associated cam disc 14. When the Schmitt-trigger 59 is reset the magnet 20 is deenergized and the striker spring 18 returns into its illustrated rest position. Thereby the stepping pawl 17 advances the associated cam disc 14 by one tooth. By this stepwise advance or rotation of the cam disc its inclined cam surface 15 slightly displaces the end 12 and consequently also the writing end 10 of the associated recording pen in axial direction. When the striker spring 18 hits the writing end of the recording pen at the end of its downward movement, the latter will mark a place on the recording tape which is slightly displaced in axial direction relatively to the original rest position of the recording pen. Each further breakdown on the same wire initiates the same effects, that is, the more breakdowns occur on a particular wire the more the recording pen is shifted by the inclined cam surface 15 and the longer the graph or record becomes which is marked in axial direction by the associated recording pen on the recording tape. Of course the same operation occurs in all channels associated each with one particular wire, so that records associated with each wire are produced.

If the counter 49 has received 10 pulses, that is, if 100 meters of wire have passed through, the relay 52 is energized. It energizes through its making contact 53 the motor 27 during a period determined by the pulse former 51, whereby the motor starts and drives the shaft 21 through toothed wheels 25 and 24 after the cam disc 28 has rotated lever 29 in counterclockwise direction and thus has removed its shoulder 32 out of the range of pin 33. The lever 29 turns the lifting beam 18 upwardly, that is, the front edge of the same is pivoted round the pivot 55 at the rear edge (at the left in FIG. 3). This pivoting movement of the lifting beam 19 causes closure of the microswitch 31 which maintains the motor circuit closed when the relay 52 is deenergized. The recording pens 10 are lifted by the lifting beam 19. The pins 22 of shaft 21 engage the cams 23 of the cam disc 14 whereby the cam discs are returned in their stepping direction into their initial position. The cam disc 8 rotates together with shaft 21 and actuates the lever 7, the ratchet wheel 4 and therewith the roller 3 and the recording tape 2 being advanced by one step. After a full revolution of motor 27 the cam disc 28 releases the lever 29 into its illustrated rest position, whereby the microswitch 31 is opened and the motor stops. The lever 29 returned to its rest position determines by its shoulder 32 the end position of the wheel 24 and of the shaft 21. Further, the lever 29 returns the lifting beam 19 and therewith the striker springs 18 and the recording pens 10 into their zero position and operating position respectively. Of course the above operation for advancing the recording tape run off very quickly so that recording of breakdowns now starts again practically without interruption.

In this way rows of transverse lines or records are produced on the recording tape, as indicated in FIG. 1 and of which each is a measure for the number of breakdowns and defects of insulation on the 100 meters of wire tested during the last counting period. As an example FIG. 1 shows in its upper portion a row of lines of which each one has the maximum length. This length is determined by approximately one full revolution of the associated cam disc 14. If the cam disc has for instance 50 teeth, the record means that the tested wire has produced at least 50 breakdowns per 100 meters. After registration of the maximum number of 50 breakdowns the cam disc 14 stops in its end position, because its toothing has a gap.

The lowermost row of lines is obtained if the varnish of the wire gradually becomes worse, wereafter a correction of the producing plant is effected. Thus, the number of breakdowns first increases and then decreases.

The second and third record from the bottom in FIG. 1 correspond to the normal case, that is, different limited numbers of breakdowns occur per recording period and per unit length of wire respectively, such numbers being within the tolerable limit.

During the operations described above all test pulleys driven by a wire running through the test station, and to which the test voltage is applied, produce a pulsating voltage at the disc 42. This voltage is amplified and applied to the rectifier 64 such that a voltage continuously exists at the condenser 65 and at the input of the Schmitt-trigger 66 by which the Schmitt-trigger 66 is maintained in a predetermined condition. With this condition gate 50 is blocked, that is, the pulses originating from switch 48 are not transmitted to the input of amplifier 60. Only the breakdowns are registered as described above. However, if no wire runs over one of the test pulleys or if no test voltage is applied to this test pulley or if it is blocked and cannot be driven by the wire, no pulsating voltage appears at the disc 42. The Schmitt-trigger 66 triggers into its other condition and opens the gate 50. In this case no pulses due to breakdowns of the test voltage, but exactly 10 pulses from the switch 48 are transmitted to the amplifier 60 and consequently to the associated electromagnet 20. Thereby similar records are produced for each recording period as shown by the fourth line from the top in FIG. 1, but such records do not attain the full hight. Such a record indicates that no wire is produced in the associated place or that the wire is not correctly tested, and the fault may be corrected.

Figure 10:
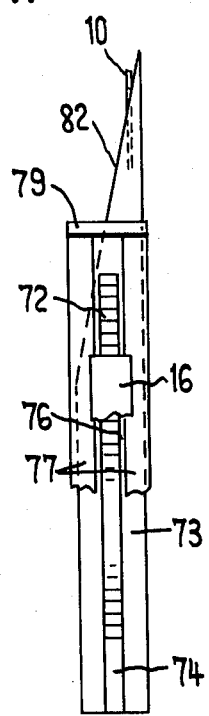
FIGS. 10 to 12 show details of a second embodiment of the apparatus.
Figure 11:
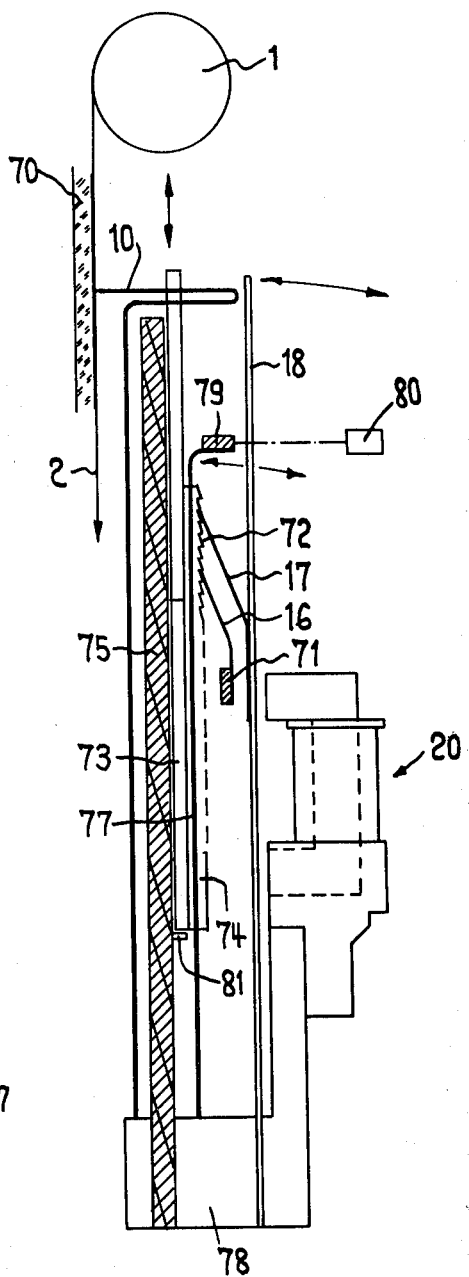
Figure 12:
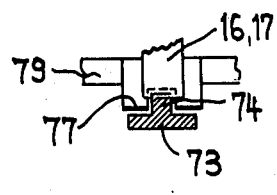

In FIGS. 10 to 12, which show the essential parts of a second embodiment, corresponding parts are similarly designated as in FIGS. 1 to 9. In this case the recording tape 2 is pulled off the roll 1 and fed downwardly at the inside of a plane viewing glass 70. The recording pen 10 of each recording unit acts upon the inner side spaced away from the viewing glass of the pressure-sensitive recording tape 2. It has been found that also with this arrangement a properly readable record is produced at the visible front side of the recording tape. The striker spring 18 to which the stepping pawl 17 is connected acts onto the recording pen 10. The striker spring 18 with the stepping pawl 17 is actuated by the magnet 20 as described.

The stop pawl 16 of each unit is fixed on a common transverse carrier 71. The pawls 16 and 17 engage a straight ratchet toothing 72 of a slide 73 of T - shaped cross section having the shape of a wedge. As shown in FIGS. 11 and 12 the springs 16 and 17 are wider than the toothed rib 74 of the slide 73. The slide 73 slides on a plate 75 and its rib 74 grips through a slit 76 of a leaf spring 77 of which the one end is fixed in a block 78 and of which the other end is connected to a beam 79 common for all units of the recorder. The beam 79 may be displaced from the illustrated rest position to the right in FIG. 10 by means of a schematically indicated electromagnet 80 or a corresponding actuating device. The slide 73 is thus displaceably guided in longitudinal direction and it may be shifted upwardly from its illustrated lower end position or rest position determined by a stop pin 81.

The slide 73 has a wedge surface 82 against which the recording pin is applied with elastical pressure.

Operation of the apparatus shown in FIGS. 10 to 12 substantially corresponds to the operation of the apparatus according to FIGS. 1 – 9, with the difference that the transverse shifting of the recording pens is effected by the wedge surface 82. By each pulse reaching the magnet 20 the striker spring is lifted as described, whereby the stepping pawl 17 is set back by one tooth in the toothing of slide 73. When the magnet is deenergized later on, the striker spring 18 hits the recording pen 10 and causes a mark on the recording tape, and the stepping pawl 17 shifts the slider 73 upwardly by one tooth division, whereby the recording pen is displaced in a direction transverse to the advancing direction of the recording tape. At the end of each test period, for instance whenever a predetermined length of wire has passed through, the magnet 80 is energized and pulls the beam 79 to the right. The spring 73 hereby engages the stepping pawl 17 and the stop pawl 16 and disengages both from the toothing 72. The slide 73 thereby falls back into its rest position. Simultaneously with the electromagnet 80 a not shown stepping device for the recording tape 2 is actuated. Recording for a further testing period may now begin.

As mentioned above, the described apparatus may be used for many similar supervising problems. Many parts of the apparatus may be designed in a different manner. Instead of a mechanical storage of the number of phenomena per test period an electrical storage may take place, this electrical storage resulting in a corresponding electromechanical or electrooptical recording at the end of the test period.

The test period must not be determined by an amount of production, but this period may correspond to a predetermined time interval, for instance in the case of trafic counting. In either case it is not absolutely necessary to stepwise advance the recording tape, because when supervising production the recording tape might be continuously advanced at a speed proportional to the speed of production and for a statistic supervision the recording tape might be advanced by a timepiece. In this case too, the number of phenomena would be recorded in a direction transverse to the advancing direction of the recording tape, but the resulting lines or traces would not extend at a right angle to the feeding direction as shown in FIG. 1 but somewhat inclined.

The indication of a fault, whether it be the absence of a wire in a production line or failure in testing for instance due to cutting out of voltage, may be effected in a different way than by counting a predetermined limited number of phenomena, or this limited number of phenomena may also be zero. In order to enable a clear distinction between a test result indicating zero faults and the indication "zero" due to missing of a wire, recording may so be effected that in all normal units a pulse is transmitted to the associated magnet 20 at the end or beginning of each test period. In the units associated with a production line without wire or without test voltage this pulse would be blocked by a gate corresponding to gate 50, such that a line of points would be recorded on the recording tape for each production line which correctly operates and is correctly supervised and where in an ideal state no faults, for instance no breakdowns occur, while no recording at all would take place for production lines which do not correctly operate.

What I claim is:

1. A method for supervising the continuous production of a product, particularly of an insulated wire, wherein a recording element is moved in a direction transverse to the advancing direction of a recording tape by a number of unit steps equal to the number of defects detected on said product during a predetermined supervising period, whereby a record is obtained the total length of which in a direction transverse to the advancing direction of the recording tape corresponds to the number of defects detected, a detecting member for detecting defects of said product being continuously moved by said product passing through a detecting station, and a failure record being produced by said recording element whenever said detecting member is no longer moved, said failure record being typical for a standstill of said detecting member and differing from any record obtained by registration of defects.

2. A method according to claim 1, wherein said failure record is obtained by advancing said recording element by the same limited number of unit steps during each supervising interval.

3. An apparatus for detecting and recording at least one record indicating a number of defects occuring during continuous production of a product, comprising a detecting member sensing said product for detecting defects, said detecting member being continuously moved by said product, a recording tape and driving means for advancing the same and a recording element controllable by said detecting member for producing at least one graphic record in a direction transverse to the advancing direction of said recording tape and in unit steps controlled each by the occurrence of a defect, and a checking device for simultaneously checking movement of said detecting member, and failure-recording means controllable by said checking device for producing a typical failure record by means of said recording element upon standstill of said detecting member.

4. An apparatus according to claim 3, wherein said failure-recording means are adapted to advance said recording member by a predetermined number of unit steps for producing a failure record of a predetermined length whenever standstill of said detecting member occurs.

5. An apparatus according to claim 3, for recording defects of the insulation on enamelled wire, wherein said detecting member is a rotatable detecting electrode, means being provided for feeding a wire over said rotatable detecting electrode, and said failure-recording means including signal transmitting means coupled with said rotatable detecting electrode, said signal transmitting means activating in its rest condition means for advancing said recording element by said predetermined number of unit steps for effecting said failure record.

6. An apparatus according to claim 5, wherein said signal transmitting means control stepping of the recording tape through a pulse counter.

* * * * *